United States Patent
Whitehurst et al.

(10) Patent No.: US 7,481,759 B2
(45) Date of Patent: Jan. 27, 2009

(54) SYSTEMS AND METHODS FOR TREATMENT OF CORONARY ARTERY DISEASE

(75) Inventors: Todd K. Whitehurst, Frazier Park, CA (US); James P McGivern, Stevenson Ranch, CA (US); Kelly H McClure, Simi Valley, CA (US); Mark R. Stultz, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 756 days.

(21) Appl. No.: 10/211,463

(22) Filed: Aug. 2, 2002

(65) Prior Publication Data

US 2003/0036773 A1    Feb. 20, 2003

Related U.S. Application Data

(60) Provisional application No. 60/310,445, filed on Aug. 3, 2001.

(51) Int. Cl.
*A61N 1/36*    (2006.01)
(52) U.S. Cl. .............................. 600/3; 607/3
(58) Field of Classification Search .............. 604/891.1; 607/120, 3
See application file for complete search history.

(56) References Cited

U.S. PATENT DOCUMENTS

| | | | |
|---|---|---|---|
| 4,080,966 A | | 3/1978 | McNally et al. |
| 4,096,866 A | * | 6/1978 | Fischell ........................ 607/34 |
| 4,922,926 A | | 5/1990 | Hirschberg et al. |
| 5,104,859 A | | 4/1992 | Sollevi |
| 5,234,404 A | | 8/1993 | Tuttle et al. |
| 5,305,745 A | * | 4/1994 | Zacouto ....................... 600/324 |
| 5,409,009 A | * | 4/1995 | Olson .......................... 600/454 |
| 5,513,644 A | | 5/1996 | McClure et al. |

(Continued)

FOREIGN PATENT DOCUMENTS

WO    WO-01/26729 A1    4/2001

OTHER PUBLICATIONS

Chari et al. "The effect of magnesium sulfate on hemodynamic and its efficacy in attenuating the response to endotracheal intubation in patients with coronary artery disease". Anesth Analg. Oct. 1998; 87(4): Abstract.*

*Primary Examiner*—Mark W Bockelman
*Assistant Examiner*—Eric D Bertram
(74) *Attorney, Agent, or Firm*—Schwegman, Lundberg & Woessner, P.A.

(57) ABSTRACT

Methods and systems for treatment of coronary artery disease (CAD) include implantation of the discharge portion(s) of a catheter and, optionally, electrodes on a lead, near the tissue(s) to be stimulated. Stimulation pulses, i.e., drug infusion pulses and optional electrical pulses, are supplied by a stimulator implanted remotely, and through the catheter or lead, which is tunneled subcutaneously between the stimulator and stimulation site. Stimulation sites include the coronary arteries, the aorta, the left ventricle, the left atrium, and/or the pulmonary veins, among other locations. Disclosed treatments include drugs used for acute treatment of CAD, for chronic treatment of CAD, to promote angiogenesis, and/or as AGE Crosslink Breakers, among other drugs. For instance, the systems and methods reduce or eliminate the incidence of CAD and related morbidities, improve symptoms resulting from CAD, and/or improve cardiac blood flow, cardiac function, and patient quality of life.

23 Claims, 4 Drawing Sheets

U.S. PATENT DOCUMENTS

| | | |
|---|---|---|
| 5,549,650 A | 8/1996 | Bornzin et al. |
| 5,551,427 A | 9/1996 | Altman |
| 5,634,895 A * | 6/1997 | Igo et al. .................... 604/21 |
| 5,634,899 A | 6/1997 | Shapland et al. |
| 5,716,937 A | 2/1998 | Haupert, Jr. |
| 5,753,517 A | 5/1998 | Brooks et al. |
| 5,840,059 A | 11/1998 | March et al. |
| 5,865,787 A | 2/1999 | Shapland et al. |
| 5,910,484 A | 6/1999 | Haupert, Jr. |
| 5,997,525 A * | 12/1999 | March et al. ............... 604/508 |
| 6,073,048 A * | 6/2000 | Kieval et al. ................ 607/17 |
| 6,112,116 A * | 8/2000 | Fischell et al. ............. 600/517 |
| 6,159,196 A * | 12/2000 | Ruiz .......................... 604/500 |
| 6,206,914 B1 * | 3/2001 | Soykan et al. ............. 623/1.42 |
| 6,228,844 B1 | 5/2001 | Wolff et al. |
| 6,358,247 B1 | 3/2002 | Altman et al. |
| 6,464,687 B1 | 10/2002 | Ishikawa et al. |
| 6,845,267 B2 * | 1/2005 | Harrison et al. ................ 607/3 |
| 2001/0044619 A1 * | 11/2001 | Altman ....................... 604/539 |
| 2002/0010492 A1 | 1/2002 | Donovan et al. |

* cited by examiner

SYSTEMS AND METHODS FOR TREATMENT OF CORONARY ARTERY DISEASE

The present application claims the benefit of U.S. Provisional Patent Application Ser. No. 60/310,445, filed Aug. 3, 2001, which application is incorporated herein by reference in its entirety.

FIELD OF THE INVENTION

The present invention generally relates to implantable drug delivery and electrical stimulation systems and methods, and more particularly relates to utilizing one or more such implantable devices for treating coronary artery disease.

BACKGROUND OF THE INVENTION

Coronary artery disease (CAD) caused over 450,000 deaths in 1997 and is the single leading cause of death in America today. Approximately 12 million Americans have a history of myocardial infarction (MI, i.e., heart attack), angina pectoris, or both. This year an estimated 1.1 million Americans will have a new or recurrent MI, and more than 40 percent will die as a result. The American Heart Association estimates the annual cost of treating CAD to be about $118.2 billion.

The major symptoms of CAD include angina pectoris and MI. Angina may be described as a discomfort, a heaviness, or a pressure in the chest. It may also be described as an aching, burning, or squeezing pain. Angina is usually felt in the chest, but may also be felt in the left shoulder, arms, neck, throat, jaw, or back. Other symptoms that can occur with CAD include:

Dyspnea (shortness of breath)
Palpitations (irregular heart beats or skipped beats)
Tachycardia (faster heart rate)
Weakness or dizziness
Nausea
Perspiration Coronary artery disease is caused by atherosclerotic narrowing of the coronary arteries. As most people age, fatty deposits form and thicken on arterial walls, causing injury to the walls of these blood vessels. Other substances floating through the bloodstream, including inflammatory cells, proteins, and calcium, stick to these injury sites. The fat and other substances combine and lead to the development of atheromas, which are complex atherosclerotic plaques consisting of lipids, fibrous tissue, collagen, calcium, cellular debris, and capillaries. As the plaque thickens, it narrows the artery. As the lumen narrows, resistance to flow increases and myocardial blood flow is compromised.

Many of these plaque deposits are hard on the outside and soft on the inside. The hard surface can crack or tear, exposing the soft, fatty inside. When this happens, platelets are activated, and a thrombus (blood clot) forms around the plaque, further narrowing the artery.

In addition to this thrombus formation initiated by platelet aggregation, the myocardium may also be injured due to CAD by one of the following mechanisms:

Progressive luminal narrowing by plaque enlargement
Hemorrhage into the atheromatous plaque
Embolization of a thrombus or plaque fragment
Coronary artery spasm A thrombus may completely block a coronary artery, causing a condition called acute coronary syndrome. This is a name for three types of CAD that are associated with sudden rupture of plaque inside a coronary artery: unstable angina, non-Q wave MI, and I wave MI. The type of acute coronary syndrome is determined by the length of time blood flow is blocked and the amount of damage that occurs. A small plaque, which may not be detectable by stress testing or cardiac catheterization, can cause an acute coronary syndrome. Prior symptoms may or may not be present.

Oxygen demand that exceeds coronary vessels' capacity can cause localized ischemia. When tissue becomes ischemic, loss of function occurs within minutes. Transient ischemia causes reversible changes at the cellular and tissue level. Lack of oxygen causes a shift from aerobic to anaerobic metabolism, which increases lactic acid production, decreases cellular pH, and increases hydrogen ion concentration. Left ventricular function is impaired, causing incomplete emptying on systole, which in turn decreases cardiac output and increases left ventricular end diastolic pressure. This may lead to increased heart rate and blood pressure (hypertension), prior to the onset of pain. This cardiovascular response is a sympathetic compensation in response to the depression of myocardial function. With pain, there is also an increase in catecholamine release. Ischemic attacks subside within minutes if the imbalance between myocyte (a.k.a., cardiac cells) supply and demand for oxygen is corrected.

As is well known in the art, the electrocardiogram (ECG) signs of impending, evolving, and completed infarction follow a course from peaked T waves to elevated ST segments, to development of Q waves, to development of T wave inversion and resolution of ST segment elevation. The abnormalities to look for are "significant" Q waves, loss of precordial R height, ST elevation in contiguous leads, and T wave peaking or inversion. Any combination of these ECG abnormalities can be present during the evolution of infarction.

Prolonged cardiac ischemia (i.e., more than 30-40 minutes) causes irreversible cellular damage and necrosis, loss of myocardial contraction, and alteration of action potential conduction. Myocardial infarction (MI) is ischemic death of myocardial tissue associated with obstruction of a coronary vessel. This myocardial area of infarction becomes necrotic due to an absolute lack of blood flow. The necrotic cells are inactive electrically and their cell membranes rupture, releasing their cellular contents into the interstitial spaces. Potassium release by these cells interferes with the electrical activity of surrounding cells and leads to arrhythmias (usually premature ventricular contractions (PVCs)).

Most episodes of myocardial ischemia leading to an acute Ml occur in the early morning hours. This may be related to diurnal rhythms of catecholamines and cortisol levels as well as enhanced platelet aggregation.

A narrowed vessel may develop collateral circulation. That is, small capillary-like branches of the artery may form over time in response to narrowed coronary arteries. The collaterals "bypass" the area of narrowing and help to restore blood flow. However, during times of increased exertion, the collaterals may not be able to supply enough oxygen-rich blood to the heart muscle.

Existing treatments for CAD suffer from a variety of disadvantages. Currently used medications tend to improve blood circulation (i.e., oxygen supply) to the heart only acutely, if at all. (Vasodilators can improve blood supply a bit.) Existing surgical procedures are invasive, have high morbidity, and/or are often only temporarily beneficial. What is needed are systems and methods to effectively and efficiently deliver drugs, possibly in combination with electrical stimulation, to appropriate treatment sites to treat CAD and relieve patients of its symptoms.

BRIEF SUMMARY OF THE INVENTION

The invention disclosed and claimed herein provides systems and methods for treating coronary artery disease (CAD) and relieving its symptoms using one or more drugs by means of a stimulator comprising an implantable pump(s) and catheter(s) and an optional implantable signal generator(s) for additionally delivering electrical stimulation. One or more catheters, and possibly also electrodes carried on a catheter or lead, are surgically implanted in the cardiovascular system supplying blood to the heart to infuse the drugs.

The present invention overcomes the shortfalls of all prior art treatment devices to achieve unprecedented levels of CAD treatment by combining administration of acute CAD medications (e.g., nitroglycerine) and chronic CAD medications (e.g., beta-adrenoceptor blockers such as carvedilol) with agents that reverse CAD, such as angiogenesis agents and agents to reverse atherosclerosis (e.g., AGE Crosslink Breakers). Additionally, the present invention optionally combines electrical stimulation with delivery of one or more of these drugs for acute (on-demand) and traditional chronic (basal or periodic bolus) treatment of CAD.

The stimulator used with the present invention possesses one or more of the following properties, among other properties:

- at least one pump and at least one catheter for delivering a drug or drugs to surrounding tissue and, optionally, at least two electrodes for applying stimulating current to surrounding tissue;
- electronic and/or mechanical components encapsulated in a hermetic package made from biocompatible material(s);
- an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the stimulator; and
- a form factor making the stimulator implantable in a target area in the body.

A stimulator may operate independently, or in a coordinated manner with other implanted stimulators, other implanted devices, and/or with devices external to a patient's body. For instance, a stimulator may incorporate means of sensing a patient's condition, e.g., a means for sensing CAD. Sensed information may be used to control the drug and/or electrical stimulation parameters of the stimulator in a closed loop manner. The sensing and stimulating means may be incorporated into a single stimulator, or a sensing means may communicate sensed information to at least one stimulator with stimulating means.

For most patients, a continuous or intermittent stimulation throughout the day is needed to provide an adequate amount of treatment. These patients may best utilize a stimulator that has a self-contained power source sufficient to deliver repeated pulses for at least several days and that can be recharged repeatedly, if necessary. In accordance with the teachings of the present invention, the use of a stimulator with a rechargeable battery thus provides these patients the portability needed to free the patient from reliance on RF power delivery. Alternatively, the power source may be a primary battery that may last several years.

For purposes of this patent application, it is sufficient to note that RF controlled stimulators receive power and control signals from an extra corporeal antenna coil via inductive coupling of a modulated RF field. Battery-operated stimulators incorporate a power source within the device itself but rely on RF control, inductive linking, or the like to program stimulus sequences and, if a rechargeable/replenishable power source is used, to recharge/replenish the power source, when needed. In accordance with the present invention, each implanted stimulator may be commanded to produce an electrical and/or infusion pulse of a prescribed magnitude and duration and at a repetition rate sufficient to treat the targeted tissue.

For instance, stimulation may be initiated by start and stop commands from a patient-governed control switch or controller, which may be handheld, containing a microprocessor and appropriate nonvolatile memory, such as electronically erasable programmable read-only-memory (EEPROM). The controller may control the implantable stimulator by any of various means. For instance, the stimulator may sense the proximity of a permanent magnet located in the controller, or may sense RF transmissions from the controller. However, it will be evident to those of skill in circuitry and computing that many different system architectures and components could be used to achieve similar functionality with either a battery-powered or RF-powered stimulator.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Acute Treatment with Medications

Acute treatment of ischemia may include either nitroglycerin (NTG) or intravenously administered magnesium sulfate ($MSO_4$). $MSO_4$ decreases the work required for breathing and reduces metabolic demand for oxygen. It also acts as a sedative to relieve anxiety and promote relaxation, and it may have a peripheral vasodilation effect, which contributes to relief of pulmonary edema. $MSO_4$ increases venous capacitance, thereby decreasing venous return, left ventricular end diastolic volume, and myocardial oxygen consumption.

NTG has a direct effect on vascular smooth muscle, resulting in generalized vasodilation, including capacitance vessels and coronary arteries. This results in reduced venous return, cardiac output, and myocardial oxygen demand. The reduced venous return also decreases left ventricular end diastolic pressure and improves blood flow to subendocardial layers of the myocardium, and may thereby increase collateral coronary blood flow.

Inhalation therapy with nitric oxide (NO) gas may also be used acutely in some symptomatic CAD patients, although this approach is currently experimental. Inhaled nitric oxide dilates pulmonary vessels, which decreases pulmonary vascular resistance and pulmonary artery pressure. It may also inhibit platelet and leukocyte function, and may modulate smooth-muscle-cell growth. If delivered directly to the coronary arteries, nitric oxide may directly dilate the coronary arteries. Nitric oxide donors (e.g., nitroprusside, nitrosothiol, organic nitrates, furoxans, sydnoimines) may also be administered, with similar effects.

Intravenous adenosine is used acutely in some symptomatic CAD patients (e.g., postoperatively), as it directly dilates coronary arteries. Adenosine also modulates platelet function, causing an antithrombotic effect, and decreases pulmonary vascular resistance and systemic vascular resistance without significant changes in systemic blood pressure. Adenosine may have significant side effects, including chest pressure/heaviness, dyspnea (shortness of breath), tingling or numbness of arms and legs, nervousness, headache, nausea, and hypotension (usually mild).

Human B-type or Brain Natriuretic Peptide (BNP, e.g., nesiritide, produced by Scios, Inc. of Sunnyvale, Calif.) is undergoing review for acute heart failure treatment. BNP possesses vasodilatory and diuretic actions. In a study of short-term heart failure treatment, it reduced pulmonary capillary wedge pressure by 20-31%.

Surgical and Other Procedural Treatment

Traditional invasive CAD treatments include PTCA (percutaneous transluminal coronary angioplasty) and CABG (coronary artery bypass graft). For PTCA (which was performed 482,000 times in 1996 in the US, at an average cost of about $20,000), a balloon catheter is inserted into the clogged artery. The inflation of this balloon in the occluded region causes the compression of the plaque, leading to a widening of the blood vessel and improved blood flow in the artery. Although deemed a successful technique by many doctors, people treated by angioplasty often suffer from restenosis, a condition involving reformation of the occluding plaque. Stents (each costing about $1,500), which are metallic tubes that sometimes help prevent the reformation of plaque, have recently been used to complement angioplasty treatment. However, the benefit of this combination over the use of angioplasty alone is debated.

For CABG (the eighth most common surgical procedure performed in the US, with 598,000 people undergoing this form of cardiac surgery in 1995), a vein or artery is harvested from another part of the body and sewn to the heart to "bypass" the occlusion. Bypasses involve highly invasive and complicated surgery, and are very expensive, at $30,000 to $40,000 per person. Not all CAD patients are candidates for PTCA or CABG. Those patients who are candidates face the risks associated with these procedures, including a 3% to 9% mortality rate during or shortly after surgery.

PTCA and CABG increase blood supply to the heart, but they do not cure CAD. Following either procedure, patients must still decrease cardiac risk factors (e.g., smoking, hypertension, high serum cholesterol) to prevent future disease.

Transmyocardial revascularization (TMR) is a procedure designed to relieve severe angina in patients who are not candidates for bypass surgery or angioplasty. During TMR, a surgeon uses a laser to drill a series of holes from the outside of the heart into the heart's pumping chamber. Twenty to forty 1 mm laser channels are created during the procedure. Bleeding from the channels stops after a few minutes of pressure from the surgeon's finger. In some patients TMR is combined with bypass surgery. How TMR reduces angina still isn't fully understood. The laser may stimulate new blood vessels to grow (angiogenesis). It may destroy nerve fibers to the heart, making patients unable to feel their chest pain. In some cases the channels may remain open, which would let oxygen-rich blood from the pumping chamber flow into the channel and then into the heart muscle.

TMR is FDA approved for use in patients with severe angina who have no other treatment options. It has also produced early promising results in three large multi-center clinical trials. The angina of 80-90 percent of patients who had this procedure has significantly improved (at least 50 percent) through one year after surgery. There's still limited follow-up data as to how long this procedure might last, however.

Chronic Treatment with Medications

A large number of medications are used to treat the symptoms and the disease process of CAD. Nitrates and nitrites, including nitroglycerin, isosorbide dinitrate, isosorbide mononitrate, and amyl nitrite are the mainstay of angina therapy. These medications decrease the myocardial oxygen requirement by relaxing vascular smooth muscle, leading to vasodilation of both arteries and veins (i.e., capacitance vessels). (Veins respond at a relatively lower nitroglycerin concentration than arteries.) Nitric oxide (NO) and NO donors (e.g., nitroprusside, nitrosothiol, organic nitrates, furoxans, sydnoimines) exert similar effects.

Other medications that are used for vasodilation and/or for treatment of angina include calcium-channel blockers (e.g., verapamil, diltiazem, bepridil, amlodipine, felodipine, isradipine, nicardipine, nifedipine, nimodipine, nisoldipine, and nitrendipine) and beta-adrenoceptor blockers (e.g., atenolol, carvedilol, esmolol, labetalol, metoprolol, nadolol, propranolol, sotalol, and timolol). (Beta-blockers block sympathetic activation of the heart through beta receptors, therefore decreasing the heart's need for extra oxygen during strenuous activity.) Cholesterol-lowering drugs may be used to retard the continuing build-up of atherosclerotic plaque, and antithrombotic agents may be employed to prevent normal blood clotting, thereby reducing the occurrence of thrombi in coronary and other arteries.

While many cardiac medications may be taken orally, others must be administered parenterally. For example, intravenous prostacyclin is approved as a treatment of certain symptoms in New York Heart Association class III/IV heart failure patients refractory to other medical therapy, and it may be administered as long-term therapy. Prostacyclin dilates pulmonary and systemic arterial and venous beds and also inhibits platelet aggregation. It may also inhibit smooth-muscle proliferation, and it may improve cardiac output and mixed venous oxygen saturation.

Kinins (e.g., bradykinin, lysylbradykinin, methionyllysylbradykinin) result in vasodilation of many arterial beds, including the coronary arteries. In contrast, kinins may result in vasoconstriction of veins. A kinin may be administered as an acute and/or chronic medication to prevent and/or treat ischemic cardiac malfunction and coronary artery stenosis.

Hypothalamic inhibitory factor (HIF) is being investigated as a potential acute and/or chronic treatment for CAD and related diseases (see, for example, U.S. Pat. No. 5,910,484). HIF has a positive inotropic effect in a whole organ preparation, such as an isolated perfused heart. HIF also dilates the coronary arteries in the isolated perfused heart as manifested in increased coronary flow in hearts treated with HIF. Thus, HIF may be used acutely or chronically to prevent and/or treat ischemic cardiac malfunction and coronary artery stenosis.

Angiogenesis and Vascular Endothelial Growth Factor (VEGF)

The growth of new blood vessels is called angiogenesis. Recently, a molecular signal that initiates angiogenesis was discovered; this substance is known as vascular endothelial growth factor (VEGF). VEGF (and similar compounds) holds great promise for CAD treatment, as it can trigger and/or accelerate the growth of collateral blood vessels. However, VEGF is not specific to cardiac tissue. Thus, in order to ensure that collateral circulation is primarily promoted in the heart, VEGF should ideally be delivered to the coronary circulation, and specifically to the artery or arteries with narrowing. VEGF may also be effective if delivered in the left atrium or ventricle, although in this case much of the medication will be shunted to the systemic circulation.

A number of studies have shown the effectiveness of sustained intra- or extra-vascular administration of VEGF for chronic myocardial ischemia in improvement of left ventricular function. For example, in 1998, Lopez, et al. investigated the efficacy of a single bolus or local intracoronary delivery of VEGF. [Lopez, et al. "VEGF administration in chronic myocardial ischemia in pigs." Cardiovascular Research, 1998 Nov; 40(2):272-81.] The observed increase in VEGF-induced perfusion correlated with improvement in regional ventricular function in all VEGF-treated groups, but not in the control animals. The authors conclude that intracoronary delivery of VEGF via bolus or subacute (3 weeks) infusion system is effective in stimulating physiologically significant angiogenesis in a porcine model of chronic myocardial ischemia.

Fibroblast Growth Factor (FGF) also acts as a potent stimulator of endothelial cell proliferation. However, unlike VEGF, FGF also stimulates the proliferation of smooth muscle cells and fibroblasts. This initially raised concerns that FGF might actually lead to the enlargement of atherosclerotic plaques primarily because of its effect on smooth muscle cell proliferation. Despite this suspected drawback, FGF has proved to be just as promising an agent for therapeutic angiogenesis as VEGF. In a canine model of coronary ischemia, increased collateral circulation was observed following intracoronary injection of basic FGF (bFGF).

Therapeutic angiogenesis may also be pursued via delivery of a gene for angiogenesis. Accelerated re-endothelialization has been demonstrated using phVEGF gene transfer, compared to recombinant VEGF protein. (phVEGF$_{165}$ is a naked plasmid DNA encoding a 165 amino acid isoform of VEGF.) A relatively low dose of protein production resulting from gene transfection is believed to offer higher degrees of safety and bioactivity than the relatively large doses of recombinant protein required for direct administration of VEGF. Several gene delivery vectors are being investigated, including naked plasmid DNA and recombinant, replication-incompetent adenoviral vectors.

U.S. Pat. No. 6,228,844 (the '844 patent) provides an example of a gene therapy agent for angiogenesis. To deliver polypeptide (such as an enzyme, hormone, growth factor, regulatory protein, or immunoregulator gene product or protein) to cardiac cells, the '844 patent introduces into the heart a carrier and a naked polynucleotide, which polynucleotide "is preferably DNA or mRNA that encodes polypeptide." Processing of the polynucleotide by, e.g., myocytes, results in expression of the gene product. Additionally, introducing mRNA according to method of the '844 patent allegedly results in "transitory expression of a polypeptide in cardiac muscle cells" lasting about one day.

Coronary Artery Disease Reversal

Aging is associated with a general increase in tissue stiffening, including the cardiovascular and bronchioalveolar systems and the skin. This aging process has been partly attributed to the crosslinking of long-lived proteins, such as collagen and elastin, initiated by the interaction of simple sugars, like glucose. This process is accelerated in those who have diabetes.

Glucose is known to react with proteins to form what are known as Advanced Glycosylation Endproducts, or AGEs. These AGEs are able to further interact with adjacent proteins to form pathological links between proteins, called AGE Crosslinks. AGE Crosslinks are prevalent in diabetic and aging individuals. Crosslinks are now considered to be likely causative factors in the development of many age-related and diabetic disorders, particularly those associated with the cardiovascular and renal systems, by causing biochemical and structural alterations to proteins. AGE Crosslinks are thought to be at least in part responsible for pathological processes of aging such as stiffening of the cardiovascular system tissues and wrinkling of the skin.

In the past there was no way to control the AGE Crosslink buildup except by keeping blood glucose levels within a normal range, and AGE Crosslink formation was believed to be irreversible. A decade ago, Alteon Pharmaceuticals (Ramsey, N.J.) was incorporated to develop an understanding of the AGE Pathway and to develop pharmaceuticals designed to interfere with the pathological consequences of AGE formation and crosslinking. Alteon has developed a new class of compounds called "thiazolium derivatives", which appear to remove the AGE Crosslinks in vivo with little or no harmful side effects. These compounds are called "AGE Crosslink Breakers".

The most promising AGE Crosslink Breaker is Alteon's ALT-711. ALT-711 breaks the specific AGE-derived crosslinks between proteins, both in vitro and in vivo. In the case of collagen, ALT-711 does not disrupt the natural enzymatic glycosylation sites or peptide bonds that are responsible for maintaining the normal integrity of the collagen chain. Thus, normal structure and function is preserved while abnormal crosslinking is reduced.

In preclinical studies at the National Institute on Aging and Johns Hopkins Geriatric Center reported in 1998, researchers demonstrated the ability of ALT-711 to reduce arterial stiffness in elderly Rhesus monkeys. Another study reported in 1998 found that diabetes-induced large artery stiffness in rats was reversed with one to three weeks of ALT-711 treatment.

In the year 2000, Dr. M. Asif, et al. reported that aged dogs treated with ALT-711 for one month demonstrated an approximately 40% reduction in age-related left ventricular stiffness. This decrease was accompanied by improvement in cardiac function. Dr. Asif, et al. posit that the decreased elasticity of the cardiovascular system that accompanies the normal aging process of mammals is due to AGE crosslinking of long-lived proteins such as collagen and lens crystallin. [Asif M, et al., "An advanced glycation endproduct cross-link breaker can reverse age-related increases in myocardial stiffness. Proceedings of the National Academy of Sciences USA, Mar. 14, 2000; 97(6):2809-13; erratum: May 9, 2000;97(10): 5679]

Sensing Cardiac Function

A number of means are available for assessing cardiac function. An ultrasound echocardiogram can non-invasively assess a number of parameters of the heart, such as left ventricle size and cardiac output. An ECG may be recorded non-invasively or invasively, and may be used to detect or diagnose a number of cardiac conditions, e.g., ischemia, arrhythmia, etc. Invasive pressure transducers may be used to determine left ventricular end diastolic pressure, pulmonary capillary wedge pressure, and systemic blood pressure. For instance, a thermal dilution catheter, the dye-dilution method, and/or catheter pressure transducers/catheter tip transducers may be used to measure blood pressure or cardiac output. Cardiac output, the total volume of blood pumped by the ventricle per minute, is the product of heart rate and stoke volume.

In a 1990 study of 21 heart transplant patients, Pepke-Zaba, et al. compared cardiac output measured by thermodilution and by impedance cardiography. They found close agreement between the measurements, both at rest and during exercise. Both measurements followed changes in heart rate and oxygen consumption. Both thermodilution and impedance cardiography methods elicited good reproducibility of cardiac output measurements at rest and during exercise. The authors concluded that the noninvasive and continuous record of cardiac output obtained by impedance cardiography can be used for the monitoring of cardiac output.

Thus, once again, existing treatments suffer from a variety of disadvantages. As stated earlier, currently used medications tend to improve blood circulation (i.e., oxygen supply) to the heart only acutely, if at all. (Vasodilators can improve blood supply a bit.) CABG is highly invasive and has high morbidity, including decrease in IQ by 10 points. PTCA is also invasive, and blood vessels may constrict again within a few months after the procedure. What is needed are systems and methods to effectively and efficiently deliver drugs to appropriate treatment sites to treat CAD and relieve patients of its symptoms.

According to the present invention, an implantable pump and catheter(s) are used to deliver one or more stimulating drugs, plus, optionally, an implantable signal generator and electrode(s) may also deliver electrical stimulation to the target area(s). One or more catheters are surgically implanted to infuse the stimulating drug(s), and, optionally, electrode(s) on a lead(s) are implanted to provide electrical stimulation.

Figure 1:
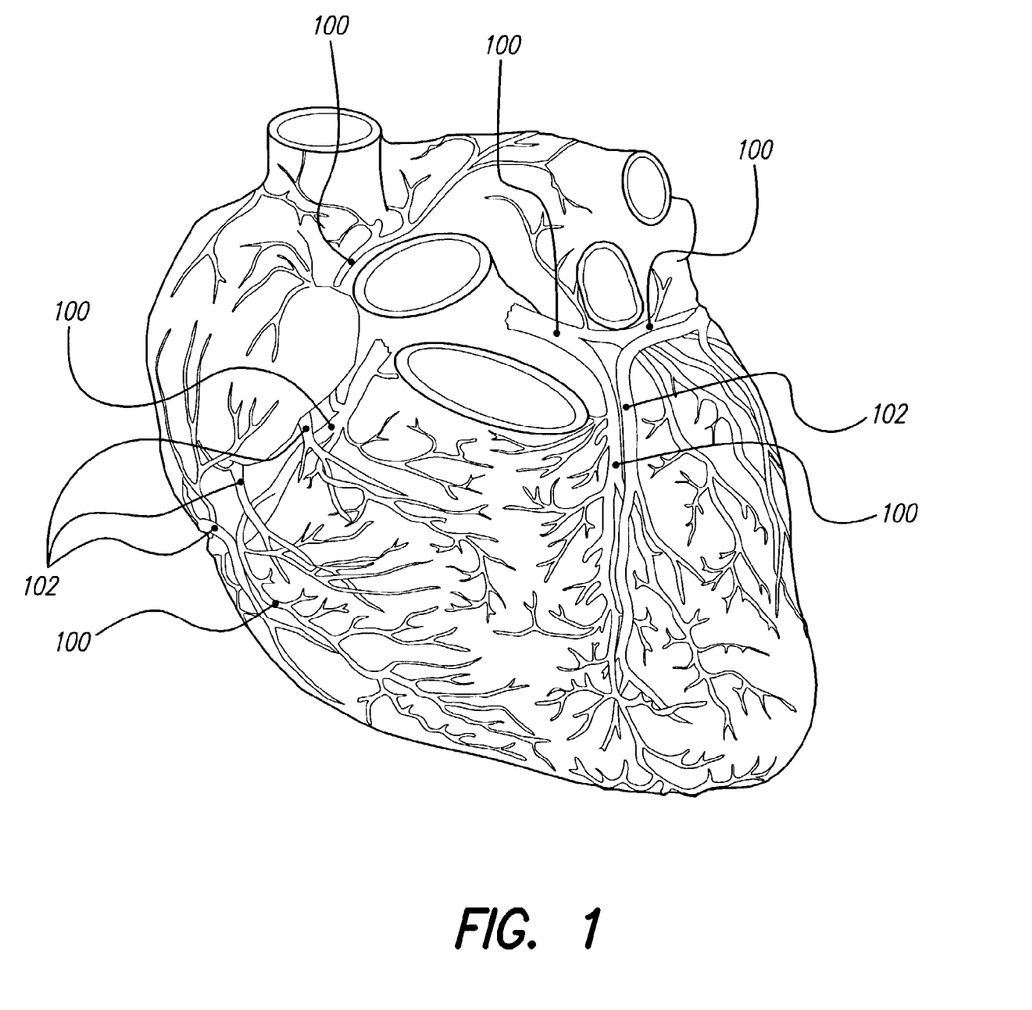
FIG. 1 is a view of the sternocostal surface of the heart.
Figure 2:
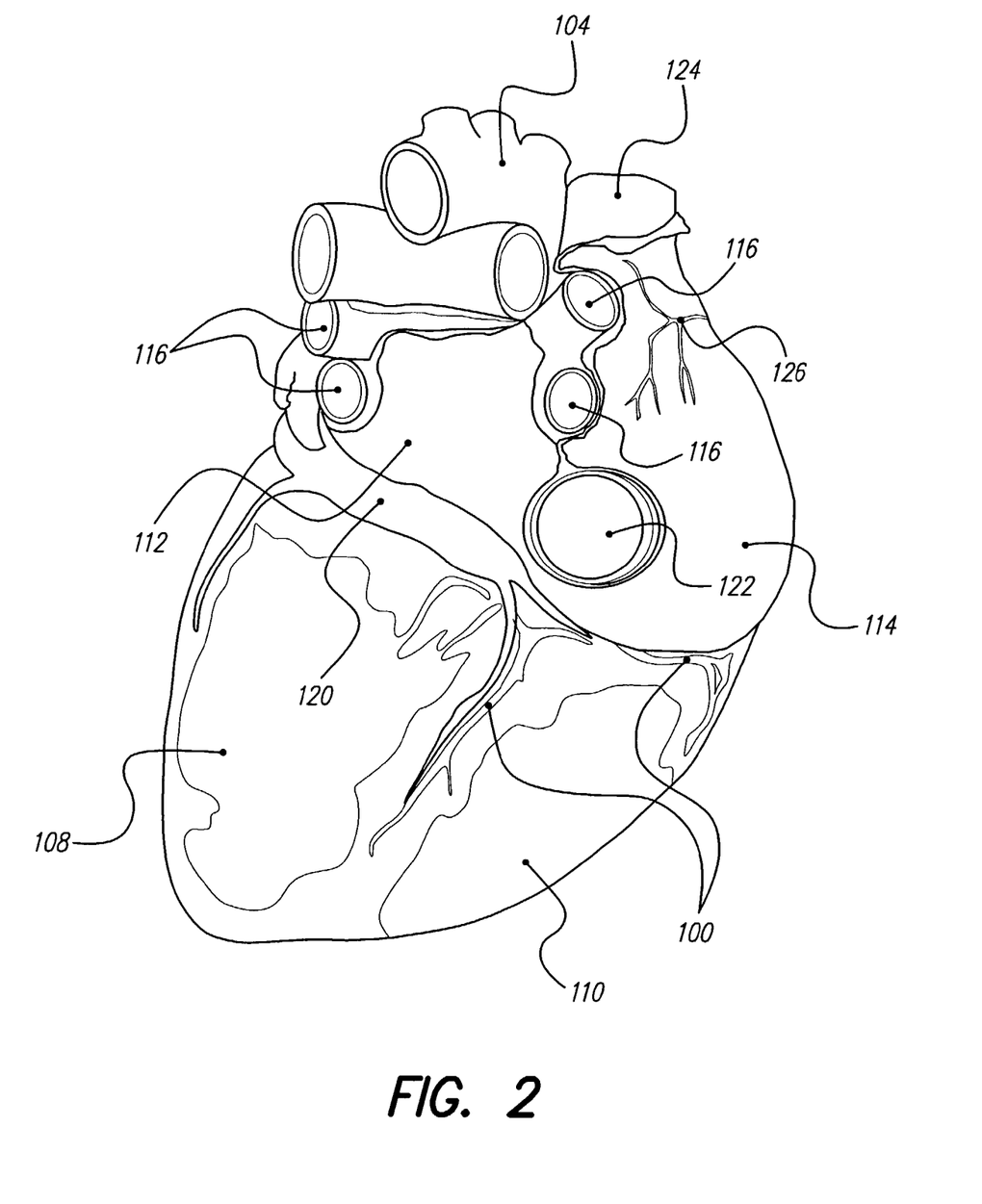
FIG. 2 is a posteroinferior view of the diaphragmatic surface of the heart.

FIG. 1 depicts the coronary arteries and the cardiac veins of the sternocostal surface of the heart, while FIG. 2 is a posteroinferior view of the diaphragmatic surface of the heart. As mentioned earlier, delivery of one or more stimulating drugs may be used to treat coronary artery disease (CAD). The drugs may be delivered to one or more of the coronary arteries 100 (which herein describes also branches of the coronary arteries), one or more of the coronary veins 102 (also including branches), the aorta 104, the left ventricle 108, the right ventricle 110, the left atrium 112, the right atrium 114, one or more of the pulmonary veins 116, the coronary sinus 120, inferior vena cava 122, superior vena cava 124, sino-atrial (SA) node 126, and/or atrio-ventricular (AV) node (not shown). Electrical stimulation may also be applied during infusion of one or more stimulating drugs.

As indicated above, the present invention is directed to systems and methods for treating CAD and relieving its symptoms. In accordance with the teachings of the present invention, one or more stimulating drugs, possibly combined with electrical stimulation, are applied to one or more of the above mentioned areas for such treatment. As used herein, stimulate, stimulation, and stimulating refer to infusion of a stimulating drug(s) and/or supplying electrical current pulses. As such, infusion parameters and/or electrical current parameters are sometimes referred to herein as simply stimulation parameters, which parameters may include amplitude, volume, pulse width, infusion rate, and the like. Similarly, stimulation pulses may be pulses of electrical energy and/or pulses of drugs infused by various means and rates of infusion, such as intermittent infusion, infusion at a constant rate, and bolus infusion.

As used herein, stimulating drugs comprise medications and other pharmaceutical compounds, anesthetic agents, synthetic or natural hormones, neurotransmitters, interleukins, cytokines, lymphokines, chemokines, growth factors, and other intracellular and intercellular chemical signals and messengers, and the like. Certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein may include stimulation of cell bodies and axons in the area.

The invention includes at least one stimulator. In the case of drug infusion only, a stimulator may comprise an implantable pump. In the case of electrical stimulation, as well, the stimulator may also comprise an implantable pulse/signal generator (IPG). In cases where both electrical stimulation and drug infusion are required or desired, more than one stimulator may be used. Alternatively, a stimulator may provide both electrical stimulation and one or more stimulating drugs.

The present invention includes a stimulator that may be implanted in a surgically-created shallow depression or opening in the thorax, abdomen, or above the buttock, that may conform to the profile of surrounding tissue(s) and/or bone(s), and is small and compact. This may minimize any cosmetic impact, and minimize pressure applied to the skin, which pressure can result in skin erosion or infection. As such, a stimulator of certain embodiments of the present invention has a diameter of about 75 mm, or only 65 mm, or even less than about 55 mm. In these configurations, stimulator thickness may be approximately 10-12 mm, or even less than 10 mm.

Figure 3:
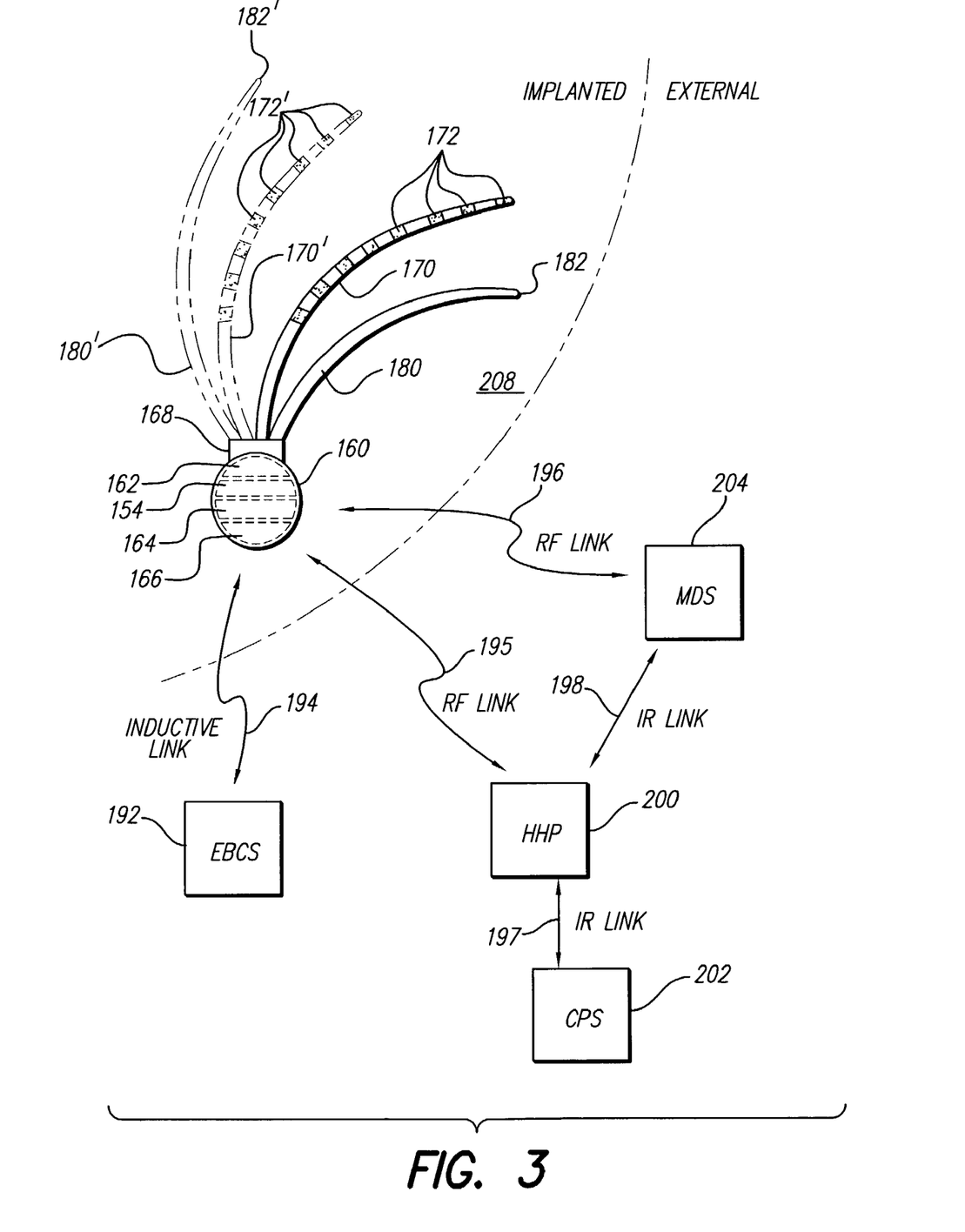
FIG. 3 illustrates an exemplary embodiment of a stimulation system of the present invention and exemplary external components of the invention.

In the exemplary embodiment of FIG. 3, one or more catheters 180 and, optionally, one or more leads 170 attach to stimulator 160 and run subcutaneously, such as in a surgically-created tunnel(s), to the tissues to be stimulated. In the case of treatment including electrical stimulation, electrode(s) 172 are carried on lead 170 having a proximal end coupled to stimulator 160. Electrode(s) 172 may include, for instance, a tip electrode and/or one or more ring electrodes, allowing, e.g., temporally synchronized stimulation. The lead contains wires electrically connecting electrodes 172 to stimulator 160. Stimulator 160 contains electrical components 154 that produce electrical stimulation pulses that travel through the wires of lead 170 and are delivered to electrodes 172, and thus to the tissue surrounding electrodes 172. Implantation of such stimulators, leads, and catheters in the locations specified herein is performed as known to those in the art, e.g., as known to interventional cardiologists.

In the case of treatment alternatively or additionally constituting drug infusion, catheter(s) 180 are coupled at a proximal end to stimulator 160, which contains at least one pump 162 for storing and dispensing one or more drug(s) through the catheter(s) 180. At or along a distal end, catheter 180 has at least one discharge portion 182 for infusing dosages of the one or more drugs into a predetermined site. Catheter 180 may also act as a lead, additionally including electrode(s) 172 at and/or along its distal end.

To protect the components inside stimulator 160, some or all of the case of the stimulator may be hermetically sealed. For additional protection against, e.g. impact, the case may be made of metal (e.g. titanium), ceramic, or the like, which materials are also, advantageously, biocompatible. The material comprising the case of the stimulator 160 may be chosen to limit passage of water vapor, while permitting passage of electromagnetic fields used to transmit data and/or power. In addition, stimulator 160 may be configured to be Magnetic Resonance Imaging (MRI) compatible.

According to embodiments as depicted in FIG. 3, at least one lead 170 and/or catheter 180 is attached to stimulator 160, via a suitable connector(s) 168, if necessary. Each lead includes at least one electrode 172, and may include as many as sixteen or more electrodes 172. Additional leads 170' and/or catheter(s) 180' may be attached to stimulator 160. Hence, FIG. 3 shows (in phantom lines) a second catheter 180', having discharge portion 182', and a second lead 170', having electrodes 172' thereon, also attached to stimulator 160.

Lead(s) 170/170' may, for instance, be less than about 5 mm in diameter, or may be even less than about 1.5 mm in diameter. Electrodes 172, 172' may be made of a noble or refractory metal or compound, such as platinum, iridium, tantalum, titanium, titanium nitride, niobium, or alloys of any of these, in order to avoid corrosion or electrolysis which could damage the surrounding tissues and/or the device. In certain embodiments, stimulator 160 is programmable to produce monopolar electrical stimulation, e.g., using the stimulator case as an indifferent electrode, or bipolar electrical stimulation, e.g., using one of the electrodes of the electrode array as an indifferent electrode. For instance, stimulator 160 may have at least four channels and may drive up to sixteen electrodes or more.

Stimulator 160 (which herein refers to implantable pump stimulators, IPG/pump combination stimulators, and/or other alternative devices known in the art) contains, when necessary and/or desired, electrical circuitry 154 (FIG. 3) for receiving data and/or power from outside the body by inductive, radio frequency (RF), or other electromagnetic coupling. In some embodiments, electrical circuitry 154 includes an inductive coil for receiving and transmitting RF data and/or power, an integrated circuit (IC) chip for decoding and storing stimulation parameters and generating stimulation pulses (either intermittent or continuous), and additional discrete components required to complete the circuit functions, e.g. capacitor(s), resistor(s), coil(s), and the like. Circuitry 154 may dictate, for instance, the amplitude and duration of the electrical current pulse, when electrical stimulation is used.

Stimulator 160 also includes, when necessary and/or desired, a programmable memory 164 for storing set(s) of data, stimulation, and control parameters. Among other things, memory 164 may allow electrical and/or drug stimulation and/or control parameters to be adjusted to settings that are safe and efficacious with minimal discomfort for each individual. Specific parameters may provide therapeutic advantages for various types and degrees of CAD. For instance, some patients may respond favorably to intermittent stimulation, while others may require continuous stimulation for treatment and relief. In some embodiments, electrical and drug stimulation parameters are controlled independently, e.g. continuous drug stimulation and no electrical stimulation. However, in some instances, they may advantageously be coupled, e.g., electrical stimulation may be programmed to occur during drug infusion.

Electrical stimulation may be applied as for cardiac pacing and/or cardiac defibrillation. Such stimulation is commonly performed by implantable devices referred to as cardiac pacemakers and implantable cardiac defibrillators (ICDs), respectively. Modern ICDs perform both the pacing and defibrillating functions. Operation of these devices, including stimulation parameters, are well-known to those skilled in the art. As another example, electrical stimulation may be applied to the vagus nerve, increasing parasympathetic stimulation to the heart, and indirectly inhibiting sympathetic stimulation. This may thus inhibit sympathetic vasoconstriction of the coronary arteries.

In addition, different parameters may have different effects on different tissue. Therefore, stimulation and control parameters may be chosen to target specific neural, muscular, and/or other cell populations and to exclude others, or to increase activity in specific neural, muscular, and/or other cell populations and to decrease activity in others. For example, relatively low frequency neurostimulation (i.e., less than about 50-100 Hz) typically has an excitatory effect on surrounding neural tissue, leading to increased neural activity, whereas relatively high frequency neurostimulation (i.e., greater than about 50-100 Hz) may have an inhibitory effect, leading to decreased neural activity.

Similarly, excitatory neurotransmitters (e.g., acetylcholine), agonists thereof, and agents that act to increase levels of an excitatory neurotransmitter(s) (e.g., edrophonium) generally have an excitatory effect on neural tissue, while inhibitory neurotransmitters (e.g., gamma-aminobutyric acid, a.k.a. GABA), agonists thereof (e.g., benzodiazepines such as lorazepam and diazepam), and agents that act to increase levels of an inhibitory neurotransmitter(s) generally have an inhibitory effect. However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g., atropine) and agents that decrease levels of excitatory neurotransmitter(s) (e.g., acetylcholinesterase) may inhibit neural activity.

Electrical stimulation parameters of, for instance, the vagus nerve will generally fall in the following ranges:
  Frequency: about 10-50 pulses per second (pps).
  Duration: about 100-500 microseconds (ps).
  Amplitude: about 0.25-10 milliamps (mA).

It is to be understood that the above ranges are not absolute. Rather, they provide a guide for stimulation parameters to be used. An attractive feature of the invention is that the stimulation parameters are programmable and can be adjusted, as required, until an appropriate and efficacious stimulation regime is achieved.

Some embodiments of stimulator 160 also include a power source and/or power storage device 166 (FIG. 3). Possible power options for a stimulation device of the present invention, described in more detail below, include but are not limited to an external power source coupled to the stimulation device (e.g., via an RF link), a self-contained power source utilizing any suitable means of generation or storage of energy (e.g., a primary battery, a replenishable or rechargeable battery such as a lithium ion battery, an electrolytic capacitor, a super- or ultra-capacitor, or the like), and if the self-contained power source is replenishable or rechargeable, means of replenishing or recharging the power source (e.g., an RF link, an optical link, a thermal link, or other energy-coupling link).

In embodiments such as depicted in FIG. 3, stimulator 160 includes a rechargeable battery as a power source/storage device 166. The battery is recharged, as required, from an external battery charging system (EBCS) 192, typically through an inductive link 194. In these embodiments, stimulator 160 includes a processor and other circuitry 154 that allow it to generate electrical/infusion pulses that are applied to a patient 208 through electrodes 172 and/or catheter(s) 180 in accordance with a program and stimulation parameters stored in programmable memory 164. As stated earlier, stimulation pulses of drugs include various types and/or rates of infusion, such as intermittent infusion, infusion at a constant rate, and bolus infusion.

According to certain embodiments of the invention, a stimulator operates independently. According to various embodiments of the invention, a stimulator operates in a coordinated manner with other stimulator(s), other implanted device(s), and/or other device(s) external to the patient's body. For instance, a stimulator may control or operate under the control of another implanted stimulator(s), other implanted device(s), and/or other device(s) external to the patient's body. A stimulator may communicate with other implanted stimulators, other implanted devices, and/or devices external to a patient's body via, e.g., an RF link, an ultrasonic link, a thermal link, and/or an optical link. Specifically, a stimulator may communicate with an external remote control (e.g., patient and/or clinician programmer) that is capable of sending commands and/or data to a stimulator and that may also be capable of receiving commands and/or data from a stimulator.

For example, in some embodiments such as shown in FIG. 3, stimulator 160 of the present invention may be activated and deactivated, programmed and tested through a hand held programmer (HHP) 200 (which may also be referred to as a patient programmer and may be, but is not necessarily, hand held), a clinician programming system (CPS) 202 (which may also be hand held), and/or a manufacturing and diagnostic system (MDS) 204 (which may also be hand held). HHP 200 may be coupled to stimulator 160 via an RF link 195. Similarly, MDS 204 may be coupled to stimulator 160 via another RF link 196. In a like manner, CPS 202 may be coupled to HHP 200 via an infra-red link 197; and MDS 204 may be coupled to HHP 200 via another infra-red link 198. Other types of telecommunicative links, other than RF or infra-red may also be used for this purpose. Through these links, CPS 202, for example, may be coupled through HHP 200 to stimulator 160 for programming or diagnostic purposes. MDS 204 may also be coupled to stimulator 160, either directly through RF link 196, or indirectly through IR link 198, HHP 200, and RF link 195.

Figure 4:
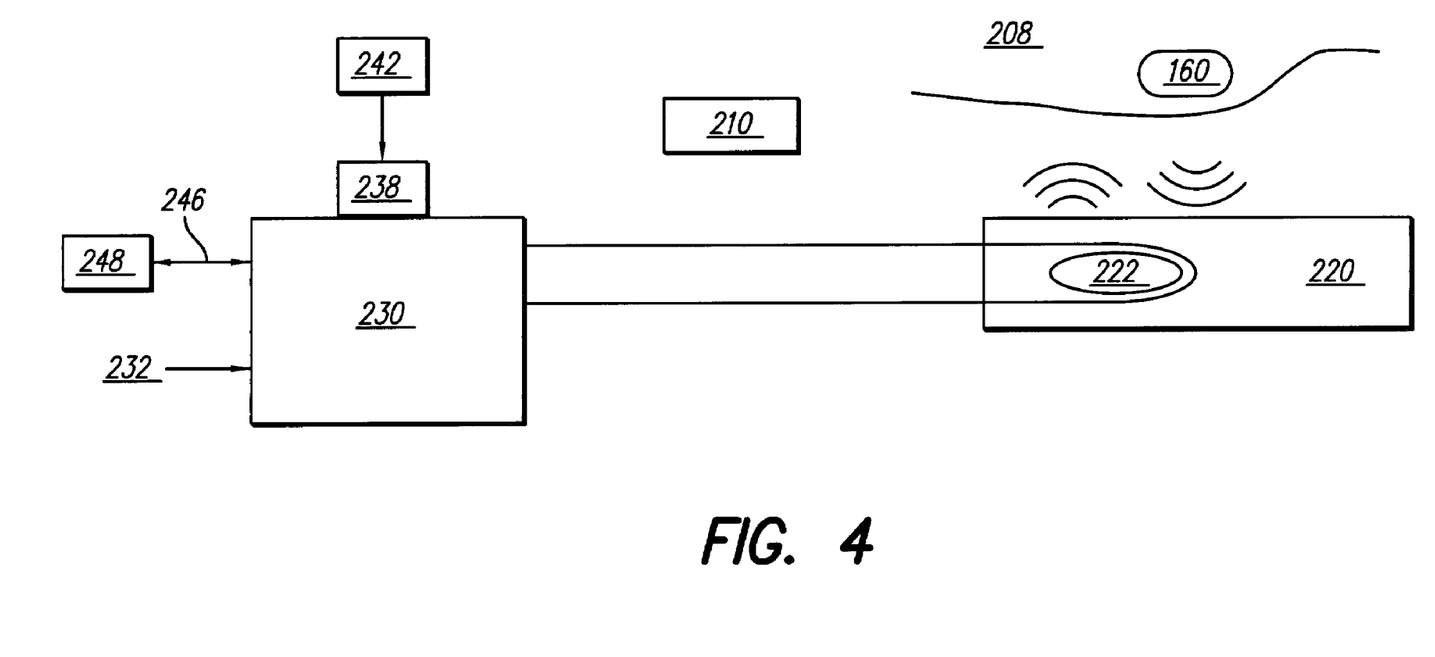
FIG. 4 illustrates an additional exemplary embodiment of external components of the invention.

In certain embodiments, and as illustrated in FIG. 4, the patient 208 switches stimulator 160 on and off by use of controller 210, which may be handheld. Stimulator 160 is operated by controller 210 by any of various means, including sensing the proximity of a permanent magnet located in controller 210, sensing RF transmissions from controller 210, or the like.

Additional and alternative exemplary external components for programming and/or providing power to various embodiments of stimulator 160 are also illustrated in FIG. 4. When communication with such a stimulator 160 is desired, patient 208 is positioned on or near external appliance 220, which appliance contains one or more inductive coils 222 or other means of communication (e.g., RF transmitter and receiver). External appliance 220 is connected to or is a part of external circuitry appliance 230 which may receive power 232 from a conventional power source. External appliance 230 contains manual input means 238, e.g., a keypad, whereby the patient 208 or a caregiver 242 may request changes in electrical and/or drug stimulation parameters produced during the normal operation of stimulator 160. In these embodiments, manual input means 238 include various electromechanical switches and/or visual display devices that provide the patient and/or caregiver with information about the status and prior programming of stimulator 160.

Alternatively or additionally, external electronic appliance 230 is provided with an electronic interface means 246 for interacting with other computing means 248, such as by a serial interface cable or infrared link to a personal computer or to a telephone modem or the like. Such interface means 246 may permit a clinician to monitor the status of the implant and prescribe new stimulation parameters from a remote location.

The external appliance(s) may be embedded in a cushion, mattress cover, garment, or the like. Other possibilities exist, including a strap, patch, or other structure(s) that may be affixed to the patient's body or clothing. External appliances may include a package that can be, e.g., worn on the belt, may include an extension to a transmission coil affixed, e.g., with a VELCRO® band or an adhesive, or may be combinations of these or other structures able to perform the functions described herein.

In order to help determine the amount and/or type(s) of stimulating drug(s), and optionally, the strength and/or duration of electrical stimulation, required to produce the desired therapeutic effect, in some embodiments, a patient's response to and/or need for treatment is sensed. For instance, the electrical activity produced in response to stimulation may be detected, e.g., via recording of the associated electrocardiograph (ECG). When catheters and/or electrodes of a stimulator are implanted, for example, in and/or near the left coronary artery or its branches, signals from an ECG sensor built into the stimulator may be used to adjust stimulation parameters. (As used herein, "adjacent" or "near" means as close as reasonably possible to target tissue(s), including touching or even being positioned within the tissue, but in general, may be as far as can be reached with the stimulation pulses).

Alternatively, a "stimulator" dedicated to sensory processes communicates with a stimulator that provides the electrical and/or infusion pulses. For instance, a microstimulator, such as a BION® manufactured by Advanced Bionics of Sylmar, Calif., may be used to detect abnormal cardiac electrocardiogram (ECG) events. For instance, a BION may use one of many algorithms for analyzing ECGs. These algorithms can operating in the frequency domain, time domain or both. They may employ linear, non-linear, or statistical analysis to categorize the electogram as originating from various modes, i.e. normal sinus rhythms, sinus tachycardia, ventricular tachycardia, and ventricular fibrillation. In addition, by finding the p, R, and T waves or analyzing the timing of the relationships and durations of the p-wave, ORS complex, and T-wave, it is possible to identify various disease states and make predictive diagnosis about perfusion of the myocardium. See, for instance, U.S. Pat. No. 5,513,644, titled "Cardiac arrhythmia detection system for an implantable stimulation device," which is incorporated herein by reference in its entirety.

In another example, the microstimulator could contain one or more accelerometers for detecting the motion of the myocardium. From analysis of the acceleration of the myocardium the contractility of the myocites may be inferred. This is also related to perfusion, and therefore is a marker for CAD. See, for instance, U.S. Pat. No. 5,549,650, titled "System and method for providing hemodynamically optimal pacing therapy," which is incorporated herein by reference in its entirety.

Addition possibilities include a microstimulator(s) or sensor(s) to detect markers of ischemia, e.g., Troponin-I or Troponin-T. See, for instance, U.S. Pat. No. 5,753,517, titled "Quantitative immunochromatographic assays," which is incorporated herein by reference in its entirety. Antibodies that bind to Troponin-I may be sensed, for instance, with a detection reagent (to which the antibodies bind) and measured using electrical conductivity or capacitance. A microstimulator or other sensor could additionally or alternatively measure an antibody that fluoresces when binding to Troponin-I, for instance, with an LED encased in a hermetic glass seal coated with the antibody.

As described below, implant circuitry 154 may, if necessary, amplify and transmit these sensed signals, which may be analog or digital. A stimulator may incorporate other means of sensing CAD, ischemia, or symptoms thereof, in order to determine the required stimulation, including sensing cardiac output, blood pressure, impedance, muscle activity (e.g., EMG), nerve activity (e.g., ENG), observing the stimulation required to decrease or eliminate pain, and/or sensing levels or changes of any blood borne substance, including medications, hormones, neurotransmitters and/or their associated breakdown products, interleukins, cytokines, lymphokines, chemokines, growth factors, enzymes, or other substances, such as CK-MB, ketones, electrolytes, blood glucose concentration, and/or other methods mentioned herein, and yet others evident to those of skill in the art upon review of the present disclosure. For instance, one or more Chemically Sensitive Field-Effect Transistors (CHEMFETs), such as Enzyme-Selective Field-Effect Transistors (ENFETs) or Ion-Sensitive Field-Effect Transistors (ISFETs, as are available from Sentron CMT of Enschede, The Netherlands), may be used. The sensed information may be used to control stimulation parameters in a closed-loop manner.

Therefore, in several embodiments of the present invention, a first and second "stimulator" are provided. The second "stimulator" periodically (e.g. once per minute) records ECG and transmits it to the first stimulator. The first stimulator uses the sensed information to adjust drug and/or electrical stimulation parameters according to an algorithm programmed, e.g., by a clinician. For example, the infusion rate of a stimulating drug, such as nitroglycerin, may be increased in response to peaked T-waves or ST elevation observed on ECG. In some alternatives, one stimulator performs both the sensing and stimulating functions, as discussed in more detail presently.

While a stimulator may also incorporate means of sensing CAD, cardiac ischemia, or symptoms thereof, e.g., via an ECG, it may alternatively or additionally be desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted stimulator(s) 160. However, in some cases, it may not be necessary or desirable to include a sensing function or device, in which case stimulation parameters are determined and refined, for instance, by patient feedback, or the like.

Thus, it is seen that in accordance with the present invention, one or more external appliances may be provided to interact with stimulator(s) 160, and may be used to accomplish, potentially among other things, one or more of the following functions:

Function 1: If necessary, transmit electrical power from the external electronic appliance 230 via appliance 220 to stimulator 160 in order to power the device and/or recharge the power source/storage device 166. External electronic appliance 230 may include an automatic algorithm that adjusts drug and/or electrical stimulation parameters automatically whenever the stimulator(s) 160 is/are recharged.

Function 2: Transmit data from the external appliance 230 via the external appliance 220 to stimulator 160 in order to change the parameters of drug and/or electrical stimulation used by stimulator 160.

Function 3: Transmit sensed data indicating a need for treatment or in response to stimulation from stimulator 160 to external appliance 230 via external appliance 220.

Function 4: Transmit data indicating state of the stimulator 160 (e.g., battery level, drug level, electrical stimulation and/or infusion settings, etc.) to external appliance 230 via external appliance 220.

By way of example, referring for example to FIG. 4, a treatment modality for CAD may be carried out according to the following sequence of procedures:

1. A stimulator 160 is implanted so that its catheter discharge portion 182 and electrodes 172 are located within the left coronary artery or its branches. If necessary or desired, additional leads 170' and/or catheters 180' may be used so that, for example, electrodes 172' and/or catheter discharge portions(s) 182' may additionally or alternatively be located in or near other coronary arteries or branches, the left ventricle, right ventricle, left atrium, right atrium, sino-atrial (SA) node, and/or atrioventricular (AV) node.

2. Using Function 2 described above (i.e., transmitting data) of external electronic appliance 230 and external appliance 220, the stimulator 160 is commanded to infuse amounts of an angiogenesis promoter, e.g., VEGF, possibly while producing a series of excitatory electrical stimulation pulses.

3. After each electrical/infusion pulse, series of stimulation pulses, or at some other predefined interval, any change in, e.g., ECG and/or cardiac output resulting from the stimulation is sensed, for instance, by one or more electrodes 172 and/or 172' acting as sensors. If necessary, these responses are converted to data and telemetered out to external electronic appliance 230 via Function 3.

4. From the response data received at external appliance 230, or from other assessment, the stimulus threshold for obtaining a response is determined and is used by a clinician 242 acting directly 238 or by other computing means 248 to transmit the desired electrical and/or drug stimulation parameters to stimulator 160 in accordance with Function 2. Alternatively, external appliance 230 makes the proper adjustments automatically, and transmits the proper stimulation parameters to stimulator 160. In yet another alternative, stimulator 160 adjusts stimulation parameters automatically based on the sensed response.

5. When patient 208 desires to invoke electrical stimulation and/or drug infusion, patient 208 employs controller 210 to set stimulator 160 in a state where it delivers a prescribed stimulation pattern from a predetermined range of allowable stimulation patterns.

6. Patient 208 employs controller 210 to turn off stimulator 160, if desired.
7. Periodically, the patient or caregiver recharges the power source/storage device 166 of stimulator 160, if necessary, in accordance with Function 1 described above (i.e., transmit electrical power).

In another example, referring now to FIG. 3, a treatment modality for CAD may be carried out according to the following sequence of procedures:
1. Stimulator 160 is implanted in the thorax, abdomen, or other remote location, and its catheter 180 and possibly also lead 170 tunneled so that its catheter discharge portion 182 and possibly also electrodes 172 are located within the left coronary artery or its branches. If necessary or desired, additional catheters 180' and/or leads 170' may be used so that, for example, catheter discharge portions(s) 182' and/or electrodes 172' may additionally or alternatively be located in or near other coronary arteries or branches, the left ventricle, right ventricle, left atrium, right atrium, sino-atrial (SA) node, and/or atrio-ventricular (AV) node.
2. Using HHP 200 described above, stimulator 160 is commanded to infuse a bolus of a vasodilator, e.g., nitroglycerin, possibly while producing a series of excitatory electrical stimulation pulses.
3. After each electrical/infusion pulse, series of stimulation pulses, or at some other predefined interval, any change in, e.g., ECG or cardiac output resulting from the stimulation is sensed, for instance, by one or more electrodes 172 and/or 172' acting as sensors. If necessary, these responses are converted to data and telemetered to HHP 200, and from there to CPS 202.
4. From the response data received at CPS 202, the stimulus threshold for obtaining a response is determined and is used by a clinician using CPS 202 and/or HHP 200 to transmit the desired electrical and/or drug stimulation parameters to stimulator 160. Alternatively, the response data are converted, if necessary, and/or used directly by stimulator 160 to modify stimulation parameters in a closed-loop manner.
5. When patient 208 desires to invoke drug and/or electrical stimulation, the patient employs HHP 200 to set stimulator 160 in a state where it delivers a prescribed stimulation pattern from a predetermined range of allowable stimulation patterns.
6. Patient 208 employs HHP 200 to turn off stimulator 160, if desired.
7. Periodically, the patient or caregiver recharges the power source/storage device 166 of stimulator 160, if necessary, using EBCS 192.

For the treatment of any of the various types and severities of CAD, cardiac ischemia, or symptoms thereof, it may be desirable to modify or adjust the algorithmic functions performed by the implanted and/or external components, as well as the surgical approaches, in ways that would be obvious to skilled practitioners of these arts. For example, in some situations, it may be desirable to employ more than one stimulator 160, each of which could be separately controlled by means of a digital address. Multiple channels and/or multiple patterns of drug and/or electrical stimulation might thereby be programmed by the clinician and controlled by the patient in order to, for instance, deal with complex or multiple symptoms or conditions, such as may occur as a result of multiple coronary artery involvement, e.g., CAD of both the left and right coronary arteries, and/or multiple cardiac diseases, e.g., CAD in combination with a cardiac arrhythmia.

In some embodiments discussed earlier, stimulator 160, or two or more stimulators, is controlled via closed-loop operation. A need for and/or response to stimulation is sensed via stimulator 160, or by an another implanted or external device. If necessary, the sensed information is transmitted to stimulator 160. In some cases, the sensing and stimulating are performed by one stimulator. In some embodiments, the parameters used by stimulator 160 are automatically adjusted based on the sensed information. Thus, the drug and/or electrical stimulation parameters may be adjusted in a closed-loop manner to provide stimulation tailored to the need for and/or response to the electrical and/or drug stimulation.

As another example, a first stimulator 160, implanted beneath the skin of the patient 208, may provide a first medication or substance; a second stimulator 160' may provide a second medication or substance; and a third stimulator 160" may provide electrical stimulation via electrodes 172 and 172'. As mentioned earlier, the implanted devices may operate independently or may operate in a coordinated manner with other similar implanted devices, other implanted devices, or other devices external to the patient's body. That is, in accordance with certain embodiments of the invention, an external device, e.g., HHP 200, CPS 202, MDS 204, controller 210, computing means 248, and/or the like, controls the operation of one or more of the implanted devices 160, 160' and 160". According to various embodiments of the invention, an implanted device, e.g., stimulator 160, may control or operate under the control of another implanted device(s), e.g., stimulator 160' and/or stimulator 160". That is, a device made in accordance with the invention may communicate with other implanted stimulators, other implanted devices, and/or devices external to a patient's body, e.g., via an RF link, an ultrasonic link, a thermal link, an optical link, or the like. Specifically, stimulator 160, 160', and/or 160", made in accordance with the invention, may communicate with an external remote control (e.g., HHP 200, CPS 202, MDS 204, computing means 248, controller 210, and/or the like) that is capable of sending commands and/or data to implanted devices and that may also be capable of receiving commands and/or data from implanted devices.

A drug infusion stimulator made in accordance with the invention may incorporate communication means for communicating with one or more external or site-specific drug delivery devices, and, further, may have the control flexibility to synchronize and control the duration of drug delivery. The associated drug delivery device typically provides a feedback signal that lets the control device know it has received and understood commands. The communication signal between the implanted stimulator and the drug delivery device may be encoded to prevent the accidental or inadvertent delivery of drugs by other signals.

Various embodiments of the present invention use one or more drugs to treat CAD acutely. According to such embodiments, one or more of the infused drugs is a medication used for acute treatment of CAD, such as nitroglycerin, magnesium sulfate, nitric oxide, a nitric oxide donor, adenosine, Atrial Natriuretic Peptide (ANP) and/or B-Type or Brain Natriuretic Peptide (BNP), such as nesiritide. Such acute medication may be delivered on demand when the patient indicates such delivery is required, such as via depression of an implanted button or via a remote control that is in communication with the stimulator. The dosage may also be programmed by a clinician, as described earlier. If the stimulator has sensing capability, also discussed earlier, such acute medication may alternatively be delivered on demand when the stimulator senses a change in cardiac function. For example, nitroglycerin might be delivered by the stimulator when it senses T wave inversion and/or ST elevation on the ECG.

Certain embodiments of the present invention use one or more drugs to treat CAD chronically. According to such embodiments, one or more of the infused drugs is a medication used for chronic treatment of CAD, such as nitroglycerin, isosorbide dinitrate, isosorbide mononitrate, amyl nitrite, nitric oxide, a nitric oxide donor, a calcium-channel blocker, a beta-blocker, a cholesterol-lowering agent, an antithrombotic agent, a kinin, prostacyclin, and/or hypothalamic inhibitory factor (HIF). Such chronic medication may be delivered at a basal rate or via periodic bolus, as programmed by a clinician. The dosage may also be programmed with other drug delivery algorithms by a clinician. Once again, sensing capabilities described earlier may be used for adjustments to chronic treatment.

Some embodiments of this invention use one or more angiogenesis drugs and/or angiogenesis promotion agents to treat CAD. According to such embodiments, one or more of the infused drugs is a medication used to promote angiogenesis, such as VEGF or FGF. In related embodiments, one or more of the infused substances is a gene that encodes a protein or other gene product that leads to angiogenesis, such as phVEGF. For instance, a polynucleotide encoding a growth factor protein or polypeptide or other angiogenesis-promoting protein or polypeptide may alternatively or additionally be infused. Such polynucleotide infusion may result in transitory expression of a polypeptide or protein lasting about one day. Agent(s) to promote angiogenesis may be delivered at a basal rate or via periodic bolus, as programmed by a clinician. The dosage or amount delivered may also be programmed with other drug delivery algorithms by a clinician. Once again, sensing capabilities described earlier may be used for adjustments to these treatments.

Various embodiments of the present invention use one or more drugs to reverse CAD. According to such embodiments, one or more of the infused drugs is an AGE Crosslink Breaker used to remove AGE Crosslinks, such as ALT-711. In related embodiments, one or more of the infused substances is a gene that encodes a protein or other gene product that leads to removal of AGE Crosslinks. Such an agent(s) to promote removal of AGE Crosslinks may be delivered at a basal rate or via periodic bolus, as programmed by a clinician. The dosage or amount delivered may also be programmed with other drug delivery algorithms by a clinician. Once again, sensing capabilities described earlier may be used for adjustments to these treatments.

Some forms of the present invention use more than one, even all, of the approaches mentioned above. As such, some combination of drug(s) to treat CAD acutely, drug(s) to treat CAD chronically, angiogenesis promotion agents, and/or AGE Crosslink Breakers/inhibitors may provide the best treatment to some patients. Once again, sensing capabilities described earlier may be used for adjustments to and timing of these treatments.

The drugs and other substances described above may be delivered via approaches, systems, and methods described earlier to one or more of the coronary arteries 100 (which herein describes also branches of the coronary arteries), one or more of the coronary veins 102 (also including branches), the aorta 104, the left ventricle 108, the right ventricle 110, the left atrium 112, the right atrium 114, one or more of the pulmonary veins 116, the coronary sinus 120, inferior vena cava 122, superior vena cava 124, sino-atrial (SA) node 126, and/or atrio-ventricular (AV) node (not shown). As discussed earlier, electrical stimulation may also be applied during infusion of one or more stimulating drugs.

Furthermore, sensing means described earlier may be used to coordinate the subacute and/or chronic treatment of CAD and related morbidities by infusion and optional electrical stimulation, and then, when appropriate, the acute treatment of CAD symptoms, e.g., significant ischemia. Alternatively, this coordination may be programmed, and not based on a sensed condition. In yet another alternative, this coordination may be controlled by the patient via the patient programmer.

While the invention herein disclosed has been described by means of specific embodiments and applications thereof, numerous modifications and variations could be made thereto by those skilled in the art without departing from the scope of the invention set forth in the claims.

What is claimed is:

1. A method for treating coronary artery disease (CAD), comprising:
    implanting a fully implantable stimulator system for generating stimulating pulses;
    acutely administering via the stimulator system stimulating pulses of at least one acute CAD drug;
    chronically administering via the stimulator system stimulating pulses of at least one chronic CAD drug; and
    administering via the stimulator system stimulating pulses of at least one drug that reverses CAD;
    wherein acutely administering via the stimulator system stimulating pulses of at least one acute CAD drug, chronically administering via the stimulator system stimulating pulses of at least one chronic CAD drug, and administering via the stimulator system stimulating pulses of at least one drug that reverses CAD are performed in combination to simultaneously administer at least two of the drugs.

2. The method of claim 1 wherein the at least one drug that reverses CAD comprises at least one of VEGF, FGF, a gene that encodes a protein or other gene product that leads to angiogenesis, phVEGF, an AGE Crosslink breaker, ALT-711, and a gene that encodes a protein or other gene product that leads to removal of AGE Crosslinks.

3. The method of claim 1 further comprising administering electrical stimulation pulses via the stimulator system to treat CAD during the delivery of one or more drugs.

4. A method of treating coronary artery disease, comprising:
    providing a stimulator that generates a pulse;
    providing a catheter connected to the stimulator;
    providing a lead connected to the stimulator;
    delivering via the stimulator and catheter infusion pulses of at least one drug as at least one treatment for coronary artery disease to at least one cardiac tissue;
    delivering via the stimulator and lead electrical stimulation pulses during the delivery of one or more stimulating drugs;
    providing at least one sensor and sensing a physical condition resulting from the delivered infusion and electrical stimulation pulses, and adjusting stimulation parameters based on the sensed condition; and
    wherein sensing a physical condition includes sensing antibodies that bind to markers of ischemia.

5. The method of claim 4, wherein delivering via the stimulator and catheter infusion pulses of at least one drug as at least one treatment for coronary artery disease to at least one cardiac tissue includes infusing a bolus of a vasodilator, and wherein delivering via the stimulator and lead electrical stimulation pulses during the delivery of one or more stimulating drugs includes producing a series of excitatory electrical stimulation pulses.

6. The method of claim 5, wherein producing a series of excitatory electrical stimulation pulses includes producing a series of excitatory electrical stimulation pulses at less than about 50-100 Hz.

7. The method of claim 4, wherein delivering via the stimulator and lead electrical stimulation pulses during the delivery of one or more stimulating drugs includes applying electrical stimulation to the vagus nerve, increasing parasympathetic stimulation to the heart, indirectly inhibiting sympathetic stimulation, and inhibiting sympathetic vasoconstriction of the coronary arteries.

8. The method of claim 7, wherein applying electrical stimulation to the vagus nerve includes delivering electrical stimulation pulses at about 10-50 pulses per second, wherein each pulse includes a pulse duration of about 100-500 microseconds and an amplitude of about 0.25- 10 milliamps.

9. The method of claim 4, wherein delivering via the stimulator and catheter infusion pulses of at least one drug as at least one treatment for coronary artery disease to at least one cardiac tissue includes delivering magnesium sulfate.

10. The method of claim 4, wherein providing at least one sensor and sensing a physical condition includes providing a microstimulator and detecting abnormal cardiac electrocardiogram events.

11. The method of claim 10, wherein detecting abnormal cardiac electrocardiogram events includes predictively diagnosing the perfusion of the myocardium by finding the p, R, and T waves of the electrocardiogram.

12. The method of claim 10, wherein detecting abnormal cardiac electrocardiogram events includes predictively diagnosing the perfusion of the myocardium by analyzing the timing of the relationships and durations of the p-wave, QRS complex, and T-wave of the electrocardiogram.

13. The method of claim 4, wherein providing at least one sensor and sensing a physical condition includes providing a microstimulator containing at least one accelerometer, detecting motion of the myocardium with the at least one accelerometer, and inferring the contractility of the myocites of the myocardium by analyzing the acceleration of the myocardium.

14. A method of treating coronary artery disease, comprising:
providing a first stimulator that generates a pulse;
providing a catheter connected to the first stimulator;
providing a lead connected to the first stimulator;
providing a second stimulator dedicated to sensory processes, wherein the second stimulator communicates with the first stimulator;
delivering via the first stimulator and catheter infusion pulses of at least one drug as at least one treatment for coronary artery disease to at least one cardiac tissue;
delivering via the first stimulator and lead electrical stimulation pulses during the delivery of one or more stimulating drugs;
sensing a physical condition with the second stimulator resulting from the delivered infusion and electrical stimulation pulses; and
adjusting stimulation parameters based on the sensed condition;
wherein delivering via the first stimulator and catheter includes:
acutely administering via the stimulator system stimulating pulses of at least one acute CAD drug;
chronically administering via the stimulator system stimulating pulses of at least one chronic CAD drug; and
administering via the stimulator system stimulating pulses of at least one drug that reverses CAD;
wherein acutely administering, chronically administering, and administering are performed in combination.

15. The method of claim 14, wherein providing a second stimulator and sensing a physical condition includes providing a micro stimulator and detecting abnormal cardiac electrocardiogram events.

16. The method of claim 15, wherein detecting abnormal cardiac electrocardiogram events includes predictively diagnosing the perfusion of the myocardium by finding the p, R, and T waves of the electrocardiogram.

17. The method of claim 15, wherein detecting abnormal cardiac electrocardiogram events includes predictively diagnosing the perfusion of the myocardium by analyzing the timing of the relationships and durations of the p-wave, QRS complex, and T-wave of the electrocardiogram.

18. The method of claim 14, wherein providing a second stimulator and sensing a physical condition includes providing a microstimulator containing at least one accelerometer, detecting motion of the myocardium with the at least one accelerometer, and inferring the contractility of the myocites of the myocardium by analyzing the acceleration of the myocardium.

19. The method of claim 18, wherein sensing a physical condition includes sensing antibodies that bind to markers of ischemia.

20. The method of claim 14, further comprising increasing the inotropic effect on the at least one cardiac tissue, wherein delivering via the first stimulator and catheter infusion pulses of at least one drug as at least one treatment for coronary artery disease to at least one cardiac tissue includes delivering via the first stimulator and catheter infusion pulses of hypothalamic inhibitory factor.

21. A method of treating coronary artery disease, comprising:
providing a stimulator that generates a pulse;
providing a catheter connected to the stimulator;
providing a lead connected to the stimulator;
delivering via the stimulator and catheter infusion pulses of at least one drug as at least one treatment for coronary artery disease to at least one cardiac tissue;
delivering via the stimulator and lead electrical stimulation pulses during the delivery of one or more stimulating drugs;
providing at least one sensor and sensing a physical condition resulting from the delivered infusion and electrical stimulation pulses, and adjusting stimulation parameters based on the sensed condition;
wherein providing at least one sensor and sensing a physical condition includes providing a microstimulator and detecting abnormal cardiac electrocardiogram events; and
wherein detecting abnormal cardiac electrocardiogram events includes predictively diagnosing the perfusion of the myocardium by finding the p, R, and T waves of the electrocardiogram.

22. A method of treating coronary artery disease, comprising:
providing a stimulator that generates a pulse;
providing a catheter connected to the stimulator;
providing a lead connected to the stimulator;

delivering via the stimulator and catheter infusion pulses of at least one drug as at least one treatment for coronary artery disease to at least one cardiac tissue;

delivering via the stimulator and lead electrical stimulation pulses during the delivery of one or more stimulating drugs;

providing at least one sensor and sensing a physical condition resulting from the delivered infusion and electrical stimulation pulses, and adjusting stimulation parameters based on the sensed condition;

wherein providing at least one sensor and sensing a physical condition includes providing a microstimulator and detecting abnormal cardiac electrocardiogram events; and wherein detecting abnormal cardiac electrocardiogram events includes predictively diagnosing the perfusion of the myocardium by analyzing the timing of the relationships and durations of the p-wave, QRS complex, and T-wave of the electrocardiogram.

23. A method of treating coronary artery disease, comprising:

providing a stimulator that generates a pulse;

providing a catheter connected to the stimulator;

providing a lead connected to the stimulator;

delivering via the stimulator and catheter infrision pulses of at least one drug as at least one treatment for coronary artery disease to at least one cardiac tissue;

delivering via the stimulator and lead electrical stimulation pulses during the delivery of one or more stimulating drugs;

providing at least one sensor and sensing a physical condition resulting from the delivered infusion and electrical stimulation pulses, and adjusting stimulation parameters based on the sensed condition; and wherein providing at least one sensor and sensing a physical condition includes providing a micro stimulator containing at least one accelerometer, detecting motion of the myocardium with the at least one accelerometer, and inferring the contractility of the myocites of the myocardium by analyzing the acceleration of the myocardium.

\* \* \* \* \*

UNITED STATES PATENT AND TRADEMARK OFFICE
CERTIFICATE OF CORRECTION

| | | |
|---|---|---|
| PATENT NO. | : 7,481,759 B2 | Page 1 of 1 |
| APPLICATION NO. | : 10/211463 | |
| DATED | : January 27, 2009 | |
| INVENTOR(S) | : Whitehurst et al. | |

It is certified that error appears in the above-identified patent and that said Letters Patent is hereby corrected as shown below:

In column 1, line 3, below "OF CORONARY ARTERY DISEASE" insert -- CROSS REFERENCE TO RELATED APPLICATION DATA --.

In column 21, line 42, in Claim 13, delete "myocites" and insert -- myocytes --, therefor.

In column 22, line 26, in Claim 18, delete "myocites" and insert -- myocytes --, therefor.

In column 24, line 4, in Claim 23, delete "infrision" and insert -- infusion --, therefor.

In column 24, line 18, in Claim 23, delete "myocites" and insert -- myocytes --, therefor.

Signed and Sealed this

Thirty-first Day of March, 2009

JOHN DOLL
*Acting Director of the United States Patent and Trademark Office*